(12) United States Patent
Gabrielsson et al.

(10) Patent No.: US 11,357,971 B2
(45) Date of Patent: Jun. 14, 2022

(54) ION PUMP WITH HYPERBRANCHED POLYMERS

(71) Applicant: OBOE IPR AB, Linköping (SE)

(72) Inventors: Roger Gabrielsson, Linköping (SE); Mats Sandberg, Linköping (SE); Magnus Berggren, Linköping (SE); Daniel Simon, Linköping (SE); David J. Poxson, Norrköping (SE); Tobias Freddie Abrahamsson, Linköping (SE)

(73) Assignee: OBOE IPR AB, Linköping (SE)

( * ) Notice: Subject to any disclaimer, the term of this patent is extended or adjusted under 35 U.S.C. 154(b) by 291 days.

(21) Appl. No.: 16/330,183

(22) PCT Filed: Sep. 5, 2017

(86) PCT No.: PCT/EP2017/072169
§ 371 (c)(1),
(2) Date: Mar. 4, 2019

(87) PCT Pub. No.: WO2018/042046
PCT Pub. Date: Mar. 8, 2018

(65) Prior Publication Data
US 2019/0224472 A1 Jul. 25, 2019

(30) Foreign Application Priority Data
Sep. 5, 2016 (SE) .................................. 1651192-5

(51) Int. Cl.
*A61N 1/30* (2006.01)
*G01N 27/447* (2006.01)
(Continued)

(52) U.S. Cl.
CPC ........... *A61N 1/0444* (2013.01); *A61N 1/303* (2013.01); *C08G 83/005* (2013.01);
(Continued)

(58) Field of Classification Search
CPC ........ A61N 1/30; A61N 1/303; G01N 27/447; G01N 27/44756; C02F 1/469–4698
See application file for complete search history.

(56) References Cited

U.S. PATENT DOCUMENTS 6,176,990 B1  1/2001  Yager et al.
6,716,948 B1  4/2004  Klaemer et al.
(Continued)

FOREIGN PATENT DOCUMENTS

EP  1862799 A1  12/2007
EP  2068146 A1  6/2009
(Continued)

OTHER PUBLICATIONS

Oudshoorn et al., "Synthesis and characterization of hyperbranched polyglycerol hydrogels," Biomaterials 27 (2006) 5471-5479 (Year: 2006).*

(Continued)

*Primary Examiner* — Alexander S Noguerola
(74) *Attorney, Agent, or Firm* — Kagan Binder, PLLC (57) ABSTRACT

A device for transport of ions and/or charged molecules between a source and a target electrolyte, comprising: a first electrode provided at or in said source electrolyte, and a second electrode provided at or in said target electrolyte; and wherein said first and second electrodes provides an electrical control of an ion flow, and further comprising means for limiting an electronic current between said source and said target electrodes, such that at least after a voltage is applied a potential difference between said source and target electrodes is maintained, which effects ion transport from said source to said target electrode; wherein the device further comprises an ion- and/or permselective polyelectrolyte for transport ions and/or charged molecules via electrophoresis and functions as an ion-selective membrane; and (Continued)

wherein said polyelectrolyte comprises a cross-linked hyperbranched polymer.

12 Claims, 7 Drawing Sheets

(51) Int. Cl.
  A61N 1/04    (2006.01)
  C08G 83/00   (2006.01)
  C08J 5/22    (2006.01)
  C08J 3/28    (2006.01)
  C08J 3/24    (2006.01)

(52) U.S. Cl.
  CPC ............ *C08G 83/006* (2013.01); *C08J 3/28* (2013.01); *C08J 5/2231* (2013.01); *C08J 5/2268* (2013.01); *G01N 27/44747* (2013.01); *G01N 27/44756* (2013.01); *C08J 3/24* (2013.01); *C08J 2300/202* (2013.01)

(56) References Cited

U.S. PATENT DOCUMENTS

| | | | |
|---|---|---|---|
| 2008/0058701 A1* | 3/2008 | Smith | A61K 9/0009 604/20 |
| 2011/0189291 A1 | 8/2011 | Yang et al. | |

FOREIGN PATENT DOCUMENTS

| | | | |
|---|---|---|---|
| EP | 2202261 | A1 | 6/2010 |
| EP | 2770568 | A1 | 8/2014 |
| EP | 2232260 | B1 | 4/2015 |
| EP | 3118613 | A1 | 1/2017 |
| GB | 2454366 | A | 5/2009 |
| JP | 2001106916 | A | 4/2001 |
| JP | 2008100941 | A | 5/2008 |
| WO | 32078110 | A2 | 10/2002 |
| WO | 2005060444 | A2 | 7/2005 |
| WO | 2008005458 | A2 | 1/2008 |
| WO | 2010017184 | A1 | 2/2010 |
| WO | 2010118754 | A1 | 10/2010 |
| WO | 2012036554 | A1 | 3/2012 |

OTHER PUBLICATIONS

Gosecki et al., Review—Polyglycidol, its Derivatives, and Polyglycidol-Containing Copolymers—Synthesis and Medical Applications, Polymers 2016, 8, 227 Published Jun. 9, 1016 (Year: 2016).*
Wyatt et al., "Degree of Branching in Hyperbranched Poly(glycerol-co-diacide)s Synthesized in Toluene," Polymers 2012, 4, 396-407 (Year: 2012).*
Hawker, "One-Step Synthesis of Hyperbranched Dendritic Polyesters," J. Am. Chem. Soc. 1991, 113, 4583-4588 (Year: 1991).*
Senol et al., "Preparation and characterization of pH-sensitive hydrogels from photo-crosslinked poly(ethylene glycol) diacrylate incorporating titanium dioxide," Materials Science-Poland, 38(3), 2020, pp. 443-449 (Year: 2020).*
Zhao, "Water soluble hyperbranched polymers from controlled radical homopolymerization of PEG diacrylate," RSC Adv., 2015, 5, 33823 (Year: 2015).*
International Search Report for International Application No. PCT/EP2017/072169, dated Nov. 15, 2017 (5 pages).
International Search Report for Swedish Application No. 1651192-5, dated May 9, 2017 (2 pages).
Poxson et al., "Regulating Plant Physiology with Organic Electronics", PNAS, vol. 114, No. 18, pp. 4597-4602, May 2, 2017, (6 pages).
Simon et al., "An Organic Electronic Ion Pump to Regulate Intracellular Signaling at High Spatiotemporal Resolution", 2009 International Solid-State Sensors, Actuators and Microsystems Conference, Denver, Jun. 21-25, 2009, (4 pages).
Jonsson et al., "Bioelectronic Neural Pixel: Chemical Stimulation and Electrical Sensing at the Same Site", Proceedings National Academy of Sciences PNAS, vol. 113, No. 34, pp. 9440-9445, Aug. 9, 2016, (10 pages).
Nieberle, "Hyperbranched Polyglycerols as Building Blocks for Complex Amphiphilic Structures: Synthesis, Characterization and Applications", Retrieved on Oct. 24, 2017 from http://publications.ub.uni-mainz.de/theses/volltexte/2012/3080/pdf/3080.pdf, (194 pages).
Ferreira et al., "Electrodialysis and Water Reuse," Novel Approaches, Springer, Berlin, Heidelberg, pp. 50-54, 2014, (8 pages).
Jones, "Perfluorosulfonic Acid Membranes for Fuel Cell and Electrolyser Applications," retrieved from 'https://www.sigmaaldrich.com/technical-documents/articles/materialsscience/perfluorosulfonic-acid-membranes.html', Copyright 2019, (9 pages).
Othman et al., "Recent Development of Polymer Electrolyte Membranes for Direct Methanol Fuel Cell Application—A Review," Malaysian Polymer Journal, vol. 5, No. 2, pp. 1-36, 2010, (36 pages).
"Energetics in Computational Simulation of Ionic Polymer," retrieved from '<http://me3007.wikidot.com/energetics-in-computational-simulation-of-ionic-polymer>', last edited on Dec. 6, 2007, (2 pages).
Sauer et al., "Auxin: simply complicated," Journal of Experimental Botany, vol. 64, No. 9, pp. 2565-2577, 2013, (13 pages).
Busch et al., "A microfluidic device and computational platform for high-throughput live imaging of gene expression," Nature Methods, vol. 9, No. 11, pp. 1101-1106, 2012, (11 pages).
Cheng et al., "Auxin biosynthesis by the YUCCA flavin monooxygenases controls the formation of floral organs and vascular tissues in Arabidopsis," GENES & DEVELOPMENT, vol. 20, pp. 1790-1799,2006, (10 pages).
Fischer et al., "Vectorial Information for Arabidopsis Planar Polarity Is Mediated by Combined AUX1, EIN2, and GNOM Activity," Current Biology, vol. 16, pp. 2143-2149, 2006 (7 pages).
Geisler et al., "Twisted DWARF1, a Unique Plasma Membraneanchored Immunophilin-like Protein, Interacts with Arabidopsis Multidrug Resistance-like Transporters AtPGPI and AtPGP19," Molecular Biology of the Cell, vol. 14, pp. 4238-4249, 2003, (12 pages).
Gonzalez-Melendi et al., "Nanoparticles as Smart Treatment-delivery Systems in Plants: Assessment of Different Techniques of Microscopy for their Visualization in Plant Tissues," Annals of Botany, vol. 101, pp. 187-195, 2008, 9 pages).
Grossmann et al., "The RootChip: An Integrated Microfluidic Chip for Plant Science," The Plant Cell, vol. 23, pp. 1234-4240, 2011, (7 pages).
Ikeda et al., "Local auxin biosynthesis modulates gradient-directed planar polarity in Arabidopsis," Nature Cell Biology vol. 11, No. 6, pp. 731-738, 2009, (24 pages).
Jaillais et al., "Unraveling the paradoxes of plant hormone signaling integration," Nature Structural & Molecular Biology, vol. 17, No. 6, pp. 642-645, 2010, (5 pages).
Meiera et al., "Chemical Stimulation of the Arabidopsis thaliana Root using Multi-Laminar Flow on a Microfluidic Chip," Lab on a Chip, vol. 10, Issue 16, pp. 2147-2153, 2010, (12 pages).
Santner et al., "Recent advances and emerging trends in plant hormone signalling," Nature, vol. 459, No. 25, pp. 1071-1078, 2009, (9 pages).
Tomalia, "The dendritic state," Materials Today, vol. 8, Issue 3, pp. 34-46, 2005, (13 pages).
Tybrandt et al., "Logic gates based on ion transistors," Nature Communications, vol. 3, No. 871, pp. 1-6, 2012, (7 pages).
Indian Office Action for Indian Counterpart Application No. 201927013662, dated Jul. 24, 2020, (6 pages).
"Matrix Delivery System," retrieved from https://www.hansvanlaarhoven.nl/matrix-delivery-system/ on Jul. 22, 2021, (5 pages).
Sunder et al., "Hyperbranched Polyether Polyols: A Modular Approach to Complex Polymer Architectures," Advanced Materials, vol. 12, No. 3, pp. 235-239, 2000, (5 pages).
Astruc et al., "Dendrimers Designed for Functions: From Physical, Photophysical, and Supramolecular Properties to Applications in (56) References Cited

OTHER PUBLICATIONS

Sensing, Catalysis, Molecular Electronics, Photonics, and Nanomedicine," Chemical Reviews, vol. 110, No. 4, pp. 1857-1959, 2010, (103 pages).

LaVan et al., "Small-scale systems for in vivo drug delivery," Nature Biotechnology, vol. 21, No. 10, pp. 1184-1191, 2003, (8 pages).

Abidjan et al., "Conducting-Polymer Nanotubes for Controlled Drug Release," Advanced Materials, vol. 18, pp. 40-5-409, 2006, (5 pages).

Xu et al., "Preparation of Monodisperse Biodegradable Polymer Microparticles Using a Microfluidic Flow-Focusing Device for Controlled Drug Delivery," Small, vol. 5, No. 13, pp. 1575-1581, 2009, (7 pages).

Svirskis et al., "Electrochemically controlled drug delivery based on intrinsically conducting polymers," Journal of Controlled Release, vol. 146, pp. 6-15, 2010, (10 pages).

Isaksson et al., "Electronic control of Ca2+ signalling in neuronal cells using an organic electronic ion pump," Nature Materials, vol. 6, pp. 673-679, 2007, (7 pages).

Tybrandt et al., "Translating Electronic Currents to Precise Acetylcholine-Induced Neuronal Signaling Using an Organic Electrophoretic Delivery Device," Advanced Materials, vol. 21, pp. 4442-4446, 2009, (5 pages).

Simon et al., "Organic electronics for precise delivery of neurotransmitters to modulate mammalian sensory function," Nature Materials, vol. 8, pp. 742-746, (2009, (5 pages).

Jonsson et al., "Therapy using implanted organic bioelectronics," Science Advances, vol. 1, No. 4, pp. 1-6, 2015, (7 pages).

Stavrinidou et al., "Direct Measurement of Ion Mobility in a Conducting Polymer," Advanced Materials, vol. 25, pp. 1488-4493, 2013, (6 pages).

Sunder et al., "Controlled Synthesis of Hyperbranched Polyglycerols by Ring-Opening Multibranching Polymerization," Macromolecules, vol. 32, No. 13, pp. 4240-4246, 1999, (7 pages).

Rahman et al., "Auxin, actin and growth of the Arabidopsis thaliana primary root," The Plant Journal, vol. 50, pp. 514-528, 2007, (15 pages).

Pencik et al., "Regulation of Auxin Homeostasis and Gradients in Arabidopsis Roots through the Formation of the ndole-3-Acetic Acid Catabolite 2-Oxindole-3-Acetic Acid," The Plant Cell, vol. 25, pp. 3858-3870, 2013, (13 pages).

Grieneisen et al., "Auxin transport is sufficient to generate a maximum and gradient guiding root growth," Nature, vol. 149, pp. 1008-1013, 2007, (6 pages).

Geisler et al., "Auxin transport during root gravitropism: transporters and techniques," Plant Biology, vol. 16, pp. 50-57, 2014, (8 pages).

Brunoud et al., "A novel sensor to map auxin response and distribution at high spatio-temporal resolution," Nature, vol. 182, pp. 103-106, 2012, (6 pages).

Friml et al., "Efflux-dependent auxin gradients establish the apical-basal axis of Arabidopsis," Nature, vol. 426, pp. 147-153, 2003, (7 pages).

Pourjavadi et al., "Novel polyelectrolyte gels as absorbent polymers for nonpolar organic solvents based on polymerizable ionic liquids," Polymer, vol. 53, pp. 5737-5742, 2012, (6 pages).

E-spacenet English Abstract and Machine Translation for JP2001106916A.

E-spacenet English Abstract and Machine Translation for JP2008100941 A.

\* cited by examiner

Fig. 6a-b

ION PUMP WITH HYPERBRANCHED POLYMERS

CROSS-REFERENCE TO RELATED APPLICATIONS

This application claims priority to International Application No. PCT/EP2017/072169, filed Sep. 5, 2017 and titled "ION PUMP WITH HYPERBRANCHED POLYMERS," which in turn claims priority from a Swedish Application having serial number 1651192-5, filed Sep. 5, 2016, and titled "ION PUMP WITH HYPERBRANCHED POLYMERS," both of which are incorporated herein by reference in their entireties.

TECHNICAL FIELD OF THE INVENTION

The present invention relates to a device for transport of ions and/or charged molecules between a source and a target electrolyte comprising a polyelectrolyte. The present invention further relates to a method for preparing a polyelectrolyte.

BACKGROUND OF THE INVENTION

In recent years, a range of organic electronic tools has been developed[1-4] which enable precise dynamic delivery of small ionic molecules.

Ion-selective electrophoretic delivery so called "ion-pumping", i.e. migration of ions through a charged membrane/gel by an electric field, is now a proven method for delivery of small molecular ions with electronic precision, as well as a good spatial and temporal control of delivery.

The organic electronic ionic pump (OEIP) is one of these technologies and was developed primarily for application to mammalian systems to enable diffusive synapse-like delivery of neurosignaling compounds (alkali ions, neurotransmitters) with high spatiotemporal resolution. Recently, OEIP devices have been demonstrated for a variety of in vitro[5,6] as well as in vivo applications[7], including therapy in awake animals[8]. OEIPs are electrophoretic delivery devices that leverage the unique ionic and electronic properties of conducting polymers and polyelectrolytes to convert electronic signals into ionic fluxes. The OEIP's polymer delivery channel (i.e., electrophoresis channel) is composed of a polycationic (or polyanionic) material with a high density of fixed charge groups that allows for the selective transport of anions (or cations). The electrophoretic transport utilized by OEIP devices is flow-free—only—the intended molecules are delivered to the target region, not additional liquid or oppositely charged counter-ions that may be present in the source solution. The selective electrophoretic transport of the desired molecular species through an OEIP device results in high concentration gradients localized at the OEIP outlet[6], on the scale of ~100 µm-1 mm. Additionally, electronic addressing to the OEIP enables the molecular delivery to be rapidly switched on and off, and importantly, the electrical driving current can be directly correlated with the ionic delivery rate. These device characteristics allow for the precise control of chemical concentration gradients with high spatial and temporal resolution.

EP 1 862 799 B1 discloses a device for electrically controlled transport of ions from a source to a target electrolyte. The device comprises a source electrode and a target electrode, each capable of conducting said ions and electrons. The source electrode is arranged to receive said ions from the source electrolyte and the target electrode is arranged to release the ions to the target electrolyte. The device further comprises an ion-conductive channel arranged to receive the ions from the source electrode, to release the ions to the target electrode and to provide an ionic connection between the source and the target electrodes. The electrodes and the ion-conductive channel are formed of solid or semi-solid materials which are directly or indirectly attached to a support. Further, the device comprises means for limiting an electronic current between the source and the target electrodes, such that at least after a voltage is applied across the channel a potential difference between the source and target electrodes is maintained, which effects ion transport from the source to the target electrode. The device comprises means for retaining one of the source and target electrolytes on the device, comprising walls for retaining the electrolyte, and being arranged such that the electrolyte is in contact with the desired electrode.

Another route to cross-linked networks, with ionic groups, is to copolymerize ionic monomers with di-functional monomers. One drawback with that route is that unreacted monomers left in the network must be removed, otherwise, ion-selectivity is lost. Post-functionalization of polyelectrolytes is a possibility, but limited by the poor solubility in solvents suitable for functionalization; polyelectrolytes are typically only soluble in water. The number of available polyelectrolyte materials suitable for OEIP device technologies is limited. It is therefore a wish for improving the current state of the art.

SUMMARY OF THE INVENTION

It is an object of the present invention to improve the current state of the art and to mitigate at least some of the above mentioned problems. These and other objects are achieved by a device for transport of ions and/or charged molecules.

According to a first aspect of the present invention there is provided a device for transport of ions and/or charged molecules between a source and a target electrolyte, comprising: a first electrode provided at or in said source electrolyte, and a second electrode provided at or in said target electrolyte; and wherein said first and second electrodes provides an electrical control of an ion flow, and further comprising means for limiting an electronic current between said source and said target electrodes, such that at least after a voltage is applied a potential difference between said source and target electrodes is maintained, which effects ion transport from said source to said target electrode; wherein the device further comprises an ion- and/or permselective polyelectrolyte for transport ions and/or charged molecules via electrophoresis and functions as an ion-selective membrane; and wherein said polyelectrolyte comprises a cross-linked hyperbranched polymer.

The present invention is based on the realization of transporting larger ions and/or charged molecules. This is realized by the use of cross-linked hyperbranched polymers. Fundamental limitations of previous devices for transporting ions and/or charged molecules can be addressed and overcome by the means of the present invention, such as swelling and rigidity of the polymer network which can be controlled by cross-linking; and transport of "larger" or reactive aromatic substances can be facilitated by tuning the void fraction distribution and effective porosity of the bulk. Example of such a device is an organic electronic ion pump (OEIP). In this application organic electronic ion pump as well as the abbreviation OEIP will be used interchangebly with device for transporting ions and/or charged molecules.

The linear polymers which are traditionally used for this kind of devices results in a tighter network as compared with the now discovered hyperbranched polymer. The tighter network results in small porous pathways and thus trough the ion-selective membrane. Hence, this type of polymers results in an ion-selective membrane that works only for smaller molecules. Moreover, the more traditional linear polymers are harder to functionalize and most often post-functionalization has to be used which results in the charges just being distributed over the surface of the network and not evenly distributed throughout the bulk.

According to at least one example embodiment of the invention hyperbranched polymers are highly branched three-dimensional (3D) macromolecules. Their spherical architectures give them unique properties such as intramolecular cavities, low viscosity and/or high solubility. Moreover, they can be equipped with plenty of functionalized groups. The cross-linked hyperbranched polymer provides large porous pathways in and through the polyelectrolyte due to their intermolecular cavities and thus through the ion-selective membrane. Crosslinking large "spherical" hyperbranched bearing crosslinkable and ionic groups, resulting in membranes and/or gels that have controllable selectivity and large porous pathways. This means that it is possible to transport larger molecules, for instance larger drug molecules such as phospholipids. The polyelectrolyte has a homogenously distributed charge. The high solubility of the hyperbranched molecules is due to their amphiphilic character.

The charges are more homogeneously spread throughout the polyelectrolyte and thereby it is possible to reduce the current needed for transporting ions trough the material as compared with the conventional OEIP. Hence, the device also provides for way of transporting smaller molecules in a more lenient manner. By avoiding large currents being used, side-reactions usually connected with these, such as water-splitting, can be avoided. Moreover, the reduced amount of current needed reduces the risk heating water. Too warm condition may cause unwished crystallization within the membrane.

The hyperbranched polymer may comprise chemical formulas 1, 2, 3,

D = Chemical formula 1
L = Chemical formula 2
T = Chemical formula 3 wherein in the chemical formulas 2 and 3, R1 is sulphonate, phosphonates or carboxylates, R2 is ammonium or phosphonium, R3 is (meth)acryloxy groups, (meth)acrylamido groups, and vinyl groups, R1, R2, R3 terminates alkyl group with C1~C20, a aryl group with C6~C20, a heteroaryl group with C2~C20, a cycloalkyl group with C6~C20, and a heterocyclic group with C2~C20. This means that the formula shown on the left side represents the hyperbranched polymer core and the final derivative is shown on the right side with crosslinkable and ionic groups.

The hyperbranched polymer may be functionalized with ketone-, aldehyde-, alcohol- and/or imine groups.

The wide variety of groups which may be used for functionalization of the hyperbranched polymer enables for a variety of properties of the material itself.

The hyperbranched polymer may have a degree of branching of 0.05-1 or a degree of branching of 0.2-0.9, or a degree of branching of 0.3-0.8, or a degree of branching of 0.4-0.8.

The degree of branching of a linear polymer would be 0. A degree of branching of 1 corresponds to a dendrimer. The properties of a hyperbranched polymer with a high degree of branching are similar to the properties of a dendrimer.

The hyperbranched polymer may be a hyperbranched polyglycerol.

Polyglycerol is a very cheap hyperbranched molecule which therefore makes it the most frequently used alternative. The monomer used for the synthesis, glycerol, is an easily achieved triol used in a variety of applications.

The molecules being pumped or transported in the device may be any one of monovalent and divalent atomic ions, multivalent biomolecules, charged aromatic molecules, and nonaromatic molecules.

As an example of mono- and di-valent atomic ions is $Na^+$, $Cl^-$. As an example of nonaromatic molecules is acetylcholine, and aromatic molecules may be for instance benzoic acid molecules. The substances or molecules being transported in the device may comprise both endogenous and synthetic substances, such as drugs. Some examples of endogenous molecules that may be transported include neurotransmitters such as gamma-aminobutyric acid (GABA) and dopamine. The molecules that may be pumped or transported through the membrane are thus molecules that are larger than what has previously been possible in the known OPEIPs.

According to at least one the device may be used for transporting auxin and/or phospholipids.

According to a second aspect there is provided a method for preparing a polyelectrolyte for a device, for transport of ions and/or charged molecules between a source and a target electrolyte comprising the steps of
i) providing a solution comprising a hyperbranched polymer having having polymerizable groups and groups that are ionic or ionizable,
ii) depositing said solution on a support; and
iii) crosslinking said hyperbranched polymer.

Effects and features of this second aspect of the present invention are largely analogous to those described above in connection with the first aspect of the inventive concept. Embodiments mentioned in relation to the first aspect of the present invention are largely compatible with the second aspect of the invention.

According to the second aspect there is further provided a method for preparing a polyelectrolyte for a device for transport of ions and/or charged molecules between a source and a target electrolyte comprising the steps of
i) providing a solution with a hyperbranched polymer having polymerizable groups and groups that are ionic or ionizable and a solvent,
ii) mixing a photoinitiator and crosslinker with said solution;
iii) depositing a support with said mixture;
iv) photo-induced curing of the deposited mixture for crosslinking of the hyperbranched polymer.

The preparation of a polyelectrolyte may thus be done as a so called "one-pot 3 component synthesis". This means that the hyperbranched polymer, the cross-linker and the photo-initiator are mixed in one solvent. This is being made possible by the solubility properties of the hyperbranched polymer. The one-pot synthesis facilitates the preparation of the polyelectrolyte and the production of the device, since the polyelectrolyte may be placed directly onto a support and then crosslinked without the necessity for further treatment steps. After the crosslink step any by products may be removed on the surface of the membrane and support. The ion conductive membrane thus filled or formed from the crosslinked hyperbranched polymer polyelectrolyte can be used in a variety of applications such as for fuel cells, electrophoresis, in microfluidics and in bio-printing.

According to at least one example embodiment of the invention the method for preparing the polyelectrolyte is divided into three steps:

The first step (i) of the polyelectrolyte is a so called one-pot synthesis. This is enabled due the amphiphilic character of the hyperbranched polymer which makes it easy to dissolve in a variety of solvents. The three components, the hyperbranched polymer, the cross-linker and the photo-initiator is mixed together before deposition of the mixture. This enables a homogeneous distribution of bulk charges.

In a following step (ii) the mixture from step i) is deposited. The one-pot synthesis as well as the amphiphilic character of the hyperbranched polymer offers a high degree of compatibility with a variety of deposition and patterning processes. The deposition method used for the preparation of the polyelectrolyte may for example be spin-coating, printing and/or any other solution based method.

After deposition the mixture will be photo-induced cured (iii). This curing may for example UV-curing.

According to an alternative there is provided a method for preparing a polyelectrolyte for a device, for transport of ions and/or charged molecules between a source and a target electrolyte, comprising the steps of
a) providing a hyperbranched polymer having polymerizable groups and groups that are ionic or ionizable;
b) adding a cross-linking agent to said hyperbranched polymer;
c) adding an initiator to hyperbranched polymer and said cross-linking agent;
d) dissolving said hyperbranched polymer, said cross-linking agent and said initiator in a solvent solution thereby forming a reagent solution;
e) allowing said hyperbranched polymer, said cross-linking agent and said initiator in said reagent solution to react with each other thereby forming a solution comprising said cross-linked hyperbranched polymer.

In the step e) of allowing said hyperbranched polymer, said cross-linking agent and said initiator in said reagent solution to react with each other, this is performed in a reaction container which is degassed and heated for a specific time.

Through this alternative method a meta-stable gels or aggregates in solution may be provided that solidifies into a solid gel upon specific concentration limits.

The hyperbranched polymer may have a degree of branching in the range of 0.05-1 or in the range of 0.1 to 1, or in the range of 0.5 to 1, or in the range of 0.7 to 1.

The method according to any one of the above methods, wherein the hyperbranched polymer comprises chemical formulas 1, 2, 3, D = Chemical formula 1
L = Chemical formula 2
T = Chemical formula 3 wherein in the chemical formulas 2 and 3, R1 is sulphonate, phosphonates or carboxylates, R2 is ammonium or phosphonium, R3 is (meth)acryloxy groups, (meth)acrylamido groups, and vinyl groups, R1, R2, R3 terminates alkyl group with C1~C20, a aryl group with C6~C20, a heteroaryl group with C2~C20, a cycloalkyl group with C6~C20, and a heterocyclic group with C2~C20.

The solvent may be any one of deionozed water, methanol, ethano, propanol, NMP, DMSO and DMF.

According to the second aspectthe the proportion of said photoinitiator and said crosslinker in step (ii) may be in the range of 0.1 to 10 parts by weight with respect to 100 parts by weight of said mixed solution.

According to a third aspect there is provided a device for transport of ions and/or charged molecules between a source and a target electrolyte, wherein said device comprises a polyelectrolyte and wherein said polyelectrolyte is synthesized according to the second aspect, and wherein said polyelectrolyte is able to transport ions and/or charged molecules via electrophoresis.

Effects and features of this third aspect of the present invention are largely analogous to those described above in connection with the first and second aspects of the inventive concept. Embodiments mentioned in relation to the first and second aspects of the present invention are largely compatible with the third aspect of the invention.

According to a fourth aspect there is provided the use of a device according to the first aspect or the third aspect for drug delivery.

BRIEF DESCRIPTION OF THE DRAWINGS

The above objects, as well as additional objects, features and advantages of the present invention, will be more fully appreciated by reference to the following illustrative and non-limiting detailed description of preferred embodiments of the present invention, when taken in conjunction with the accompanying drawings, wherein.

DETAILED DESCRIPTION OF THE DRAWINGS

In the present detailed description, embodiments of the present invention will be discussed with the accompanying figures. It should be noted that this by no means limits the scope of the invention, which is also applicable in other circumstances for instance with other types or variants of devices for transporting ions and/or charged molecules than the embodiments shown in the appended drawings. Further, that specific features are mentioned in connection to an embodiment of the invention does not mean that those components cannot be used to an advantage together with other embodiments of the invention. The embodiments described below are merely examples of possible device architectures and the present invention should not be limited thereto. The scope of the invention is as defined by the appended claims. The term "ion" as used herein encompasses not only positively or negatively charged monovalent or multivalent ionic species of atomic elements, but also other molecular species carrying a net positive or negative charge. Hence, in an embodiment of the invention it is intended to transport charged biologically active molecules or macromolecules such as charged amino acids, DNA, DNA sequences/fragments or plasmids, proteins, vitamins, peptides or hormones. In one embodiment of the invention, the ions that may be transported are cations, for example metal ions, such as potassium or calcium ions. In another embodiment of the invention the ions that may be transported are anions. The transported "ions" may act as stimuli for the cells. These stimuli may turn on a cellular process or turn off a cellular process, or act as an inhibitor. A non-limiting example is potassium which may act as stimuli for neuronal cells by opening the voltage-operated Ca2+ channels in the cell membrane. A non-limiting example of an inhibitor may be cadmium which may block the voltage-operated Ca2+ channels in the cell membrane. The term ion also encompasses species that may be charged by setting a certain pH of the electrolyte solution or channel. The pH needed to charge these species may be calculated from the pKa of these molecules. The term ion also encompasses molecules which may be chemically modified to obtain a net charge, e.g. by attaching an ion to them. ion-conductive channel used in the invention is made of a solid or semi-solid material which is able to conduct ions. According to one embodiment of the invention the ion-conductive channel may be essentially electronically nonconductive, i.e. the capability of conducting electrons is substantially limited. The general configuration of an organic electronic ion pump (OEIP) has been described in the art. In for instance EP2232260B1 a general description of the production and the configuration of an OEIP is provided. The substrate onto which the OEIP may be placed, or printed i.e. be fabricated preferably is electrically and ionically insulating and may comprise rigid materials such as Si wafers with an insulating oxide (SiOx) or nitride layer (Si3N4), glass wafers such as pyrex wafers, glass substrates, such as microscope slides, plastic substrates such as PET, polystyrene, used in petri dishes, and ceramics. The substrates may also be flexible such as plastic films, Orgacon films (both plastic and paper), or paper based materials. The ion transport device according to the invention is also particularly advantageous in that it can be easily realized on a support, such as polymer film or paper. Thus, the different components can be deposited on the support by means of conventional printing techniques such as screen printing, offset printing, gravure printing, ink-jet printing and flexographic printing, or coating techniques such as knife coating, doctor blade coating, extrusion coating and curtain coating. The ion-conductive channel or membrane (ion channel), may thus be deposited through in situ polymerization and crosslinking. An aspect of the invention provides such processes for the manufacture of an ion transport device from the materials specified herein. The device, comprising electrodes and the ion conductive membrane may be directly or indirectly attached to a solid support such as glass or to a flexible support such as polymer film or paper. The ion transport device according to the invention may preferably be encapsulated, in part or entirely, for protection of the device. The device according to the invention may also present further features, which facilitate use of the device. Such features include for example terminals for connecting a voltage source to the electrodes of the device, means for encapsulating the device in order to make it more robust to handling, and to prevent evaporation or contamination of liquid electrolytes. The general configuration of an OEIP as described in for instance EP2232260 may be used also for the production and configuration of a device according to the present invention. Below is described a number of embodiments comprising the hyperbranched polymer having has polymerizable groups and groups that are ionic or ionizable, wherein the hyperbranched polymer is crosslinked, and forming a polyelectrolyte for the delivery of different molecules such as drugs.

Figure 1:
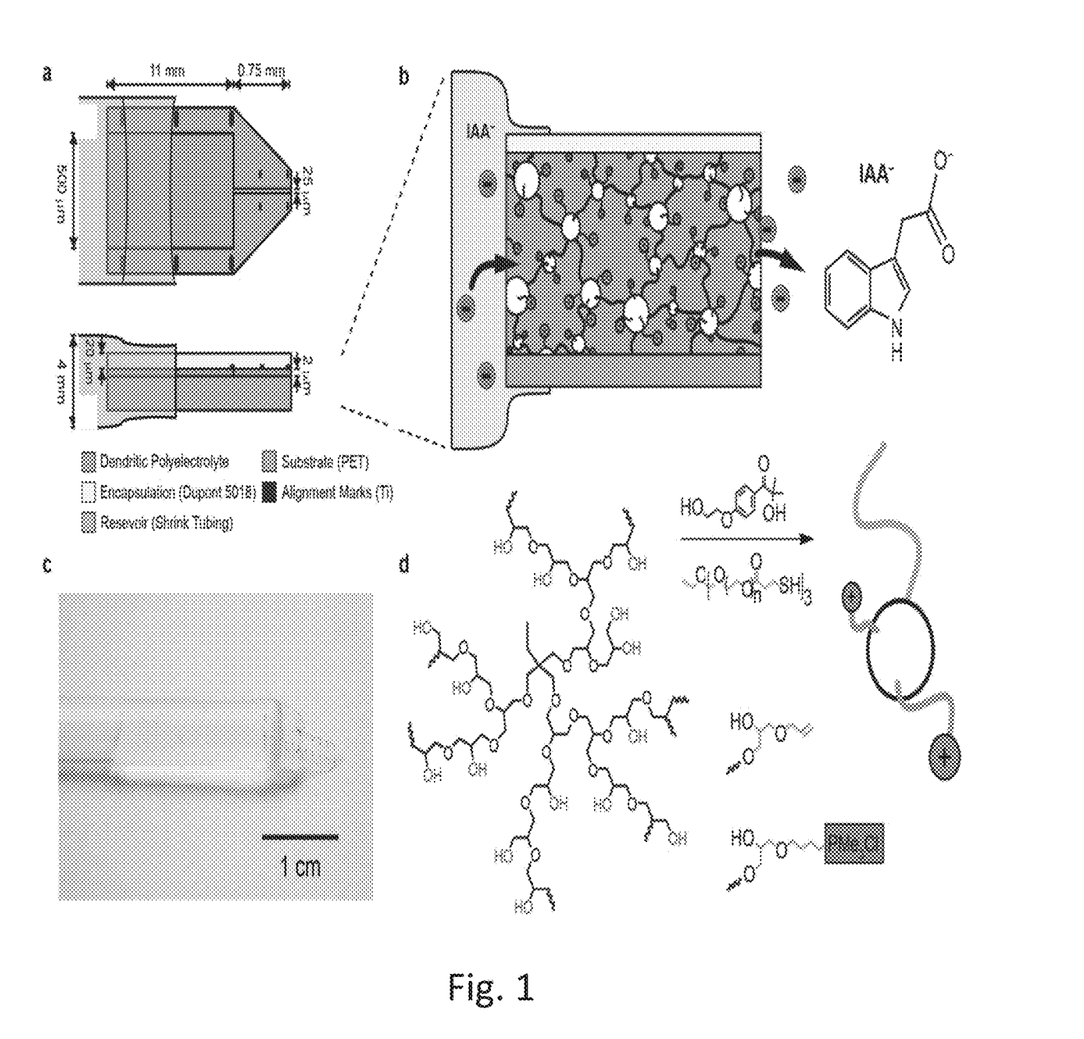
FIG. 1 shows schematic diagrams representing different features of the invention in accordance with at least one embodiment of the invention.

FIG. 1 illustrates a design of an organic electronic ion pump (OEIP) delivering auxin in vitro. FIG. 1a is a schematic diagrams of a OEIP device materials and geometries. FIG. 1b is a schematic diagram of a conceptualization of the cationic dendric polyglycerol polyelectrolyte membrane. Anionic species such as auxin indole-3-acetic acid (IAA) are selectively transported and migrate through the ion conducting channel in proportion to the applied potential gradient. FIG. 1c is a photograph of the fully fabricated OEIP device. FIG. 1d illustrates dendric polyglycerol-based polyelectrolyte system showing crosslinking (green), terminal groups (orange), and positive charge functionalization (blue).

Figure 2:
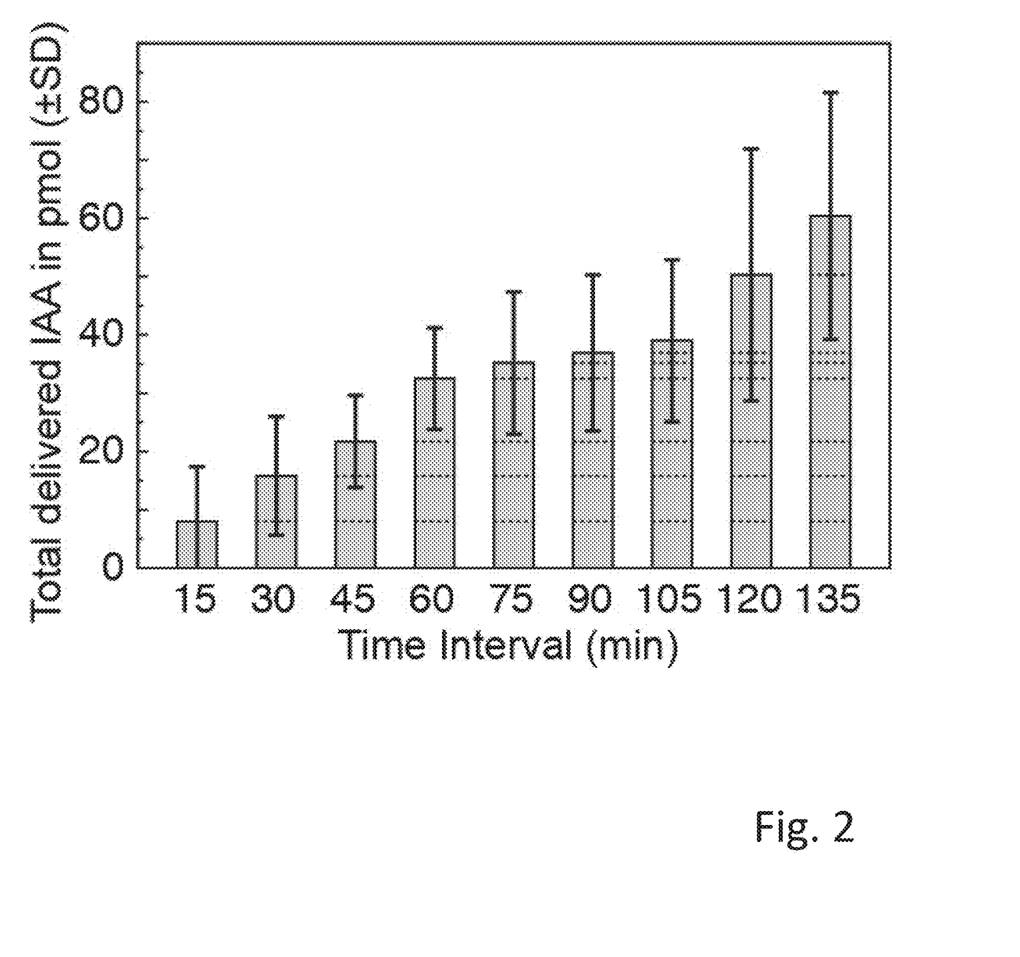
FIG. 2 shows a diagram of the total OEIP-delivered auxin as a function of time in accordance with at least one embodiment of the invention.

FIG. 2 illustrates the IAA delivered via OEIP. Total (summed) OEIP-delivered auxin vs time, e.g., 30 min timepoint is sum of 15 min measurement plus 30 min measurement (as marked by dot-lines). Error bars indicate standard deviation.

Figure 3A:
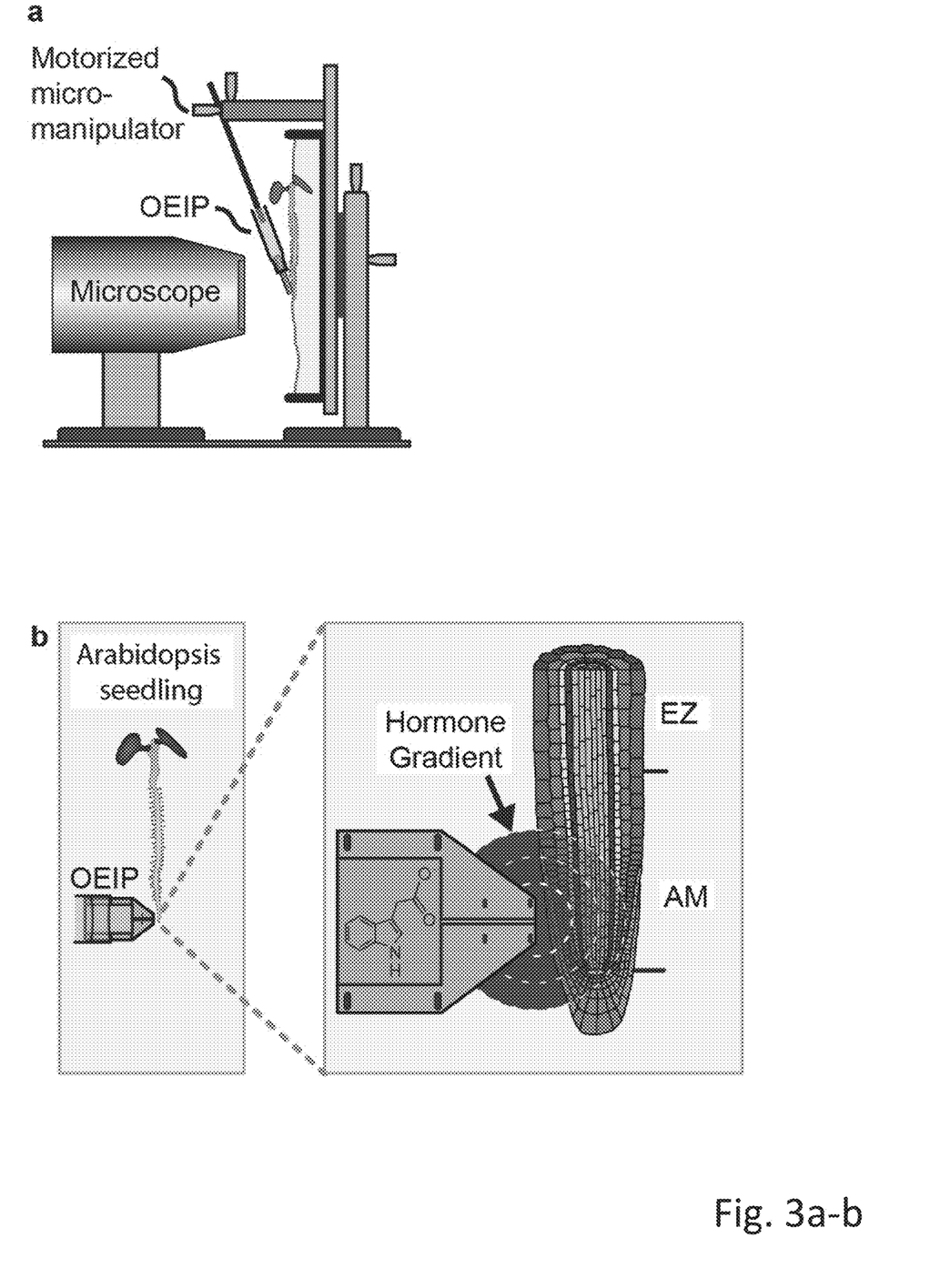
FIG. 3 shows an in vivo set-up at seedling roots and mounting on vertical macroscope stage in accordance with at least one embodiment of the invention.
Figure 3C:
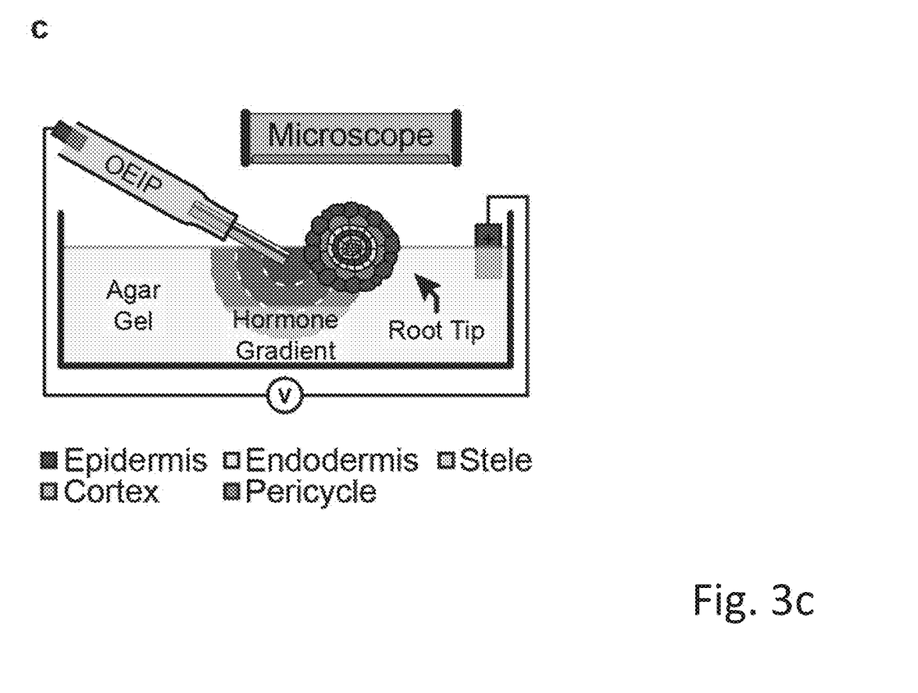

FIG. 3 illustrates an in vivo set-up at seedling roots and mounting on vertical macroscope stage. FIG. 3a shows an OEIP mounted to a motorized micro-manipulator and A. thaliana plant seedlings positioned vertically on growth-agar plates. FIG. 3b shows an OEIP positioned in proximity to the seedling root apical meristem (AM) and elongation zone (EZ). FIG. 3c, OEIP delivery tip and root cross section shown submerged in the growth agar gel. Delivery of IAA is pictured as a diffusive concentration gradient from the OEIP delivery tip through the agar gel and exogenous to the root tissue.

Figure 4A:
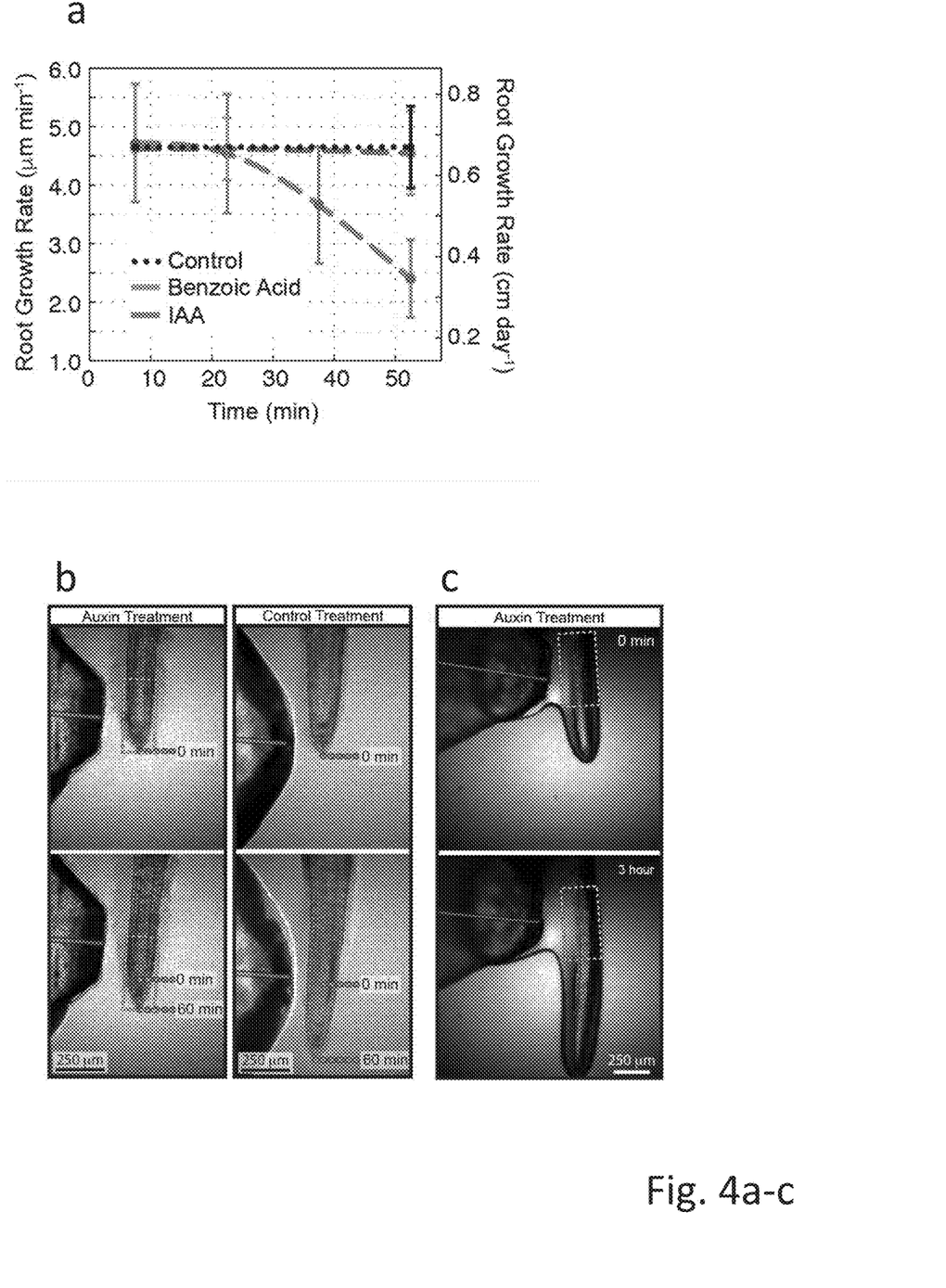
FIG. 4 shows OEIP-mediated root growth in accordance with at least one embodiment of the invention.

FIG. 4 shows an OEIP-mediated root growth inhibition by auxin. Bright field images at different time intervals during continuous OEIP delivery of IAA. The position of the 25 μm wide polyelectrolyte channel is highlighted in green. FIG. 4a shows the growth rate of DII-Venus root tips are plotted as a function of OEIP delivery time (Averages±SEM from n=5 independent treatments are displayed from a time interval of 15 min) of IAA, benzoic acid, and for non-targeted control. FIG. 4b shows the reduction in growth rate can be observed during delivery of IAA compared to benzoic acid negative control over the same time interval. Start and end root tip positions are indicated with blue dashed lines, image area matching 5b highlighted. FIG. 4c, DR5 seedlings with image area matching FIG. 5c highlighted. Scale bar 250 μm.

Figure 5A:
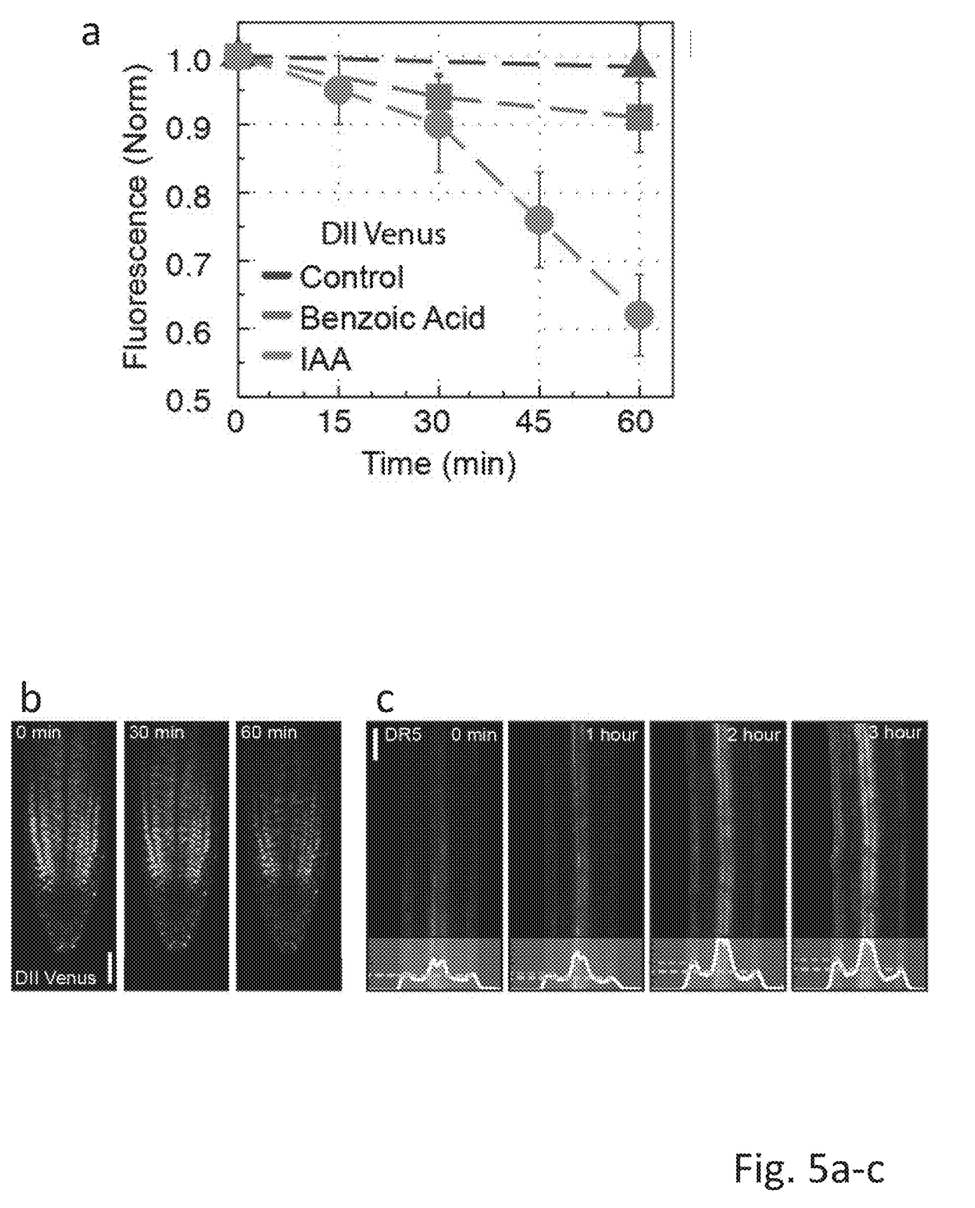
FIG. 5 shows imaging of OEIP-induced auxin responses in accordance with at least one embodiment of the invention.

FIG. 5 illustrates the imaging of OEIP-induced auxin responses. FIG. 5a shows the fluorescence intensity of DII-Venus reporter seedlings plotted for OEIP delivery of IAA, benzoic acid, and non-targeteted. Averages±SEM from n=5 independent treatments are displayed. FIG. 5b shows the confocal fluorescent image sequence of the root tip of DII-Venus reporter seedling at intervals 0, 30, 60 min. FIG. 5c shows the confocal fluorescent image sequence of the elongation zone of DR5rev:GFP reporter seedlings at intervals 0, 1, 2, and 3 h. Image intensities were summed from 16 z-stack layers with 3 μm spacing. Lateral fluorescent intensity across the root elongation zone is summed vertically, normalized and superimposed. Scale bars, 50 μm. Images are representative of five roots treated.

FIG. 6 illustrates the synthetic method for achieving one example of a hyperbranched polymer. Here, the hyperbranched polymer is a dendritic hyperbranched polyglycerols (dPG). In the figure the dPG is marked HBPG (hyperbranched polyglycerol). The synthetic route to dPGs having negative (anionic), sulfonic acid, and allyl groups for crosslinking is outlined in FIG. 6. The density of stationary ionic and cross-linking points in dPG's are controlled by the degree of substitution for the appropriate groups. The process for formation of the crosslinked dPGs is also crucial. We have opted for photo-initiated radical coupling in inert atmosphere to generate stable covalent groups forming the membrane/gels. A high conversion of the cross-linking and binding to the substrate is necessary to provide the cohesive and adhesive strength of the channel to withstand the stress of exposure to lithographic process media, as well as the operation environment.

Figure 6A:
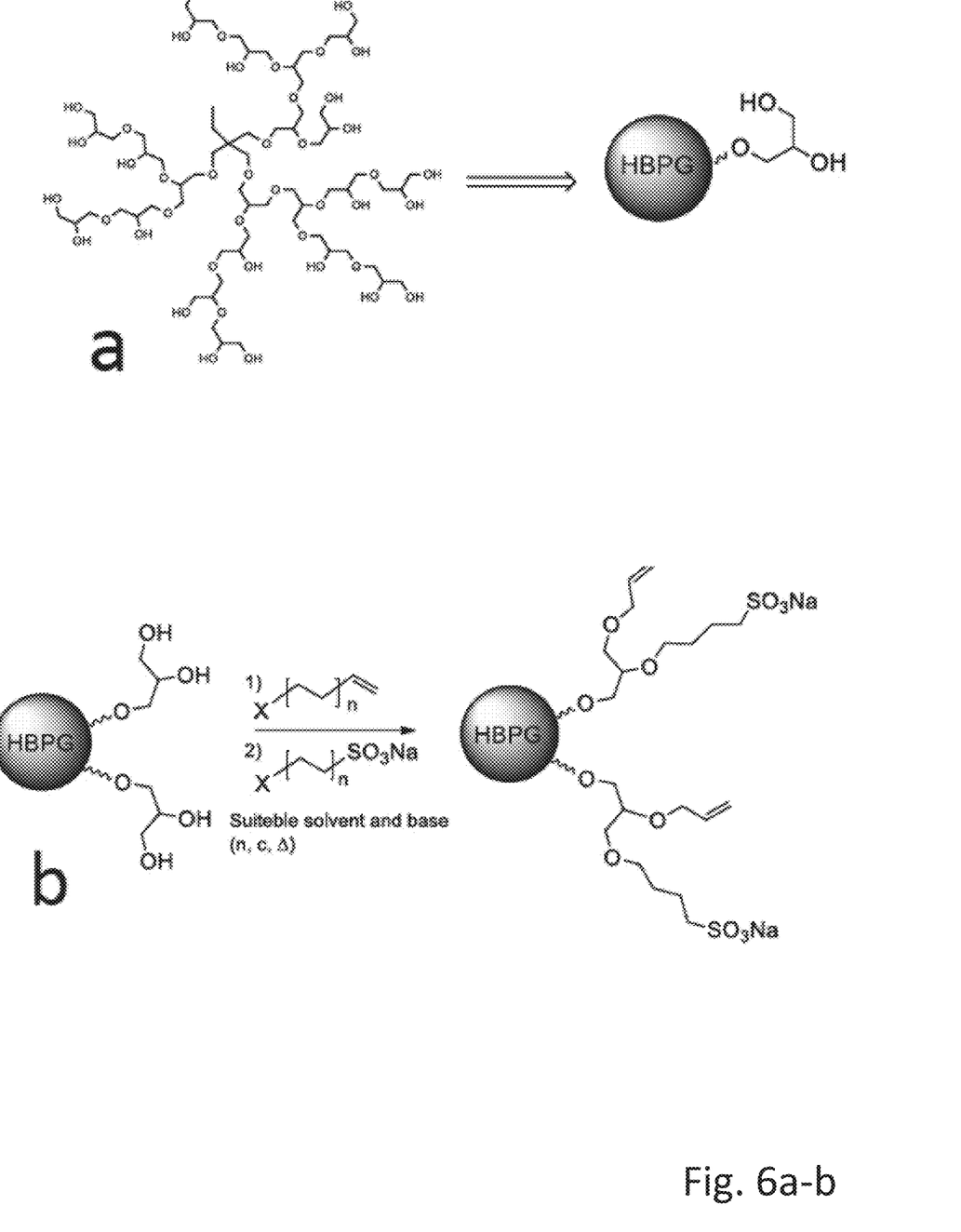
FIG. 6 shows a schematic scheme for the synthesis of the hyperbranched polymer in accordance with at least one embodiment of the invention.

FIG. 6a illustrates the schematics over the core material used in the synthesis, dendritic hyperbranched polyglycerol of molecular weight 10 kDa. FIG. 6b illustrates the schematics over the synthesis of the functionalized dPGs with allyl- and sulfonate groups.

The skilled person realizes that a number of modifications of the embodiments described herein are possible without departing from the scope of the invention, which is defined in the appended claims.

EXAMPLES

To address the need for OEIP technologies capable of transporting larger ionic compounds, hyperbranched polymers were investigated as the foundation for a new class of polyelectrolyte materials. Hyperbranched polymers are generally spherical and possess a high number of terminal functional groups that define their customizable physiochemical properties[10]. Hyperbranched polymers based on homogenous, flexible polyether alcohols (e.g., dendritic hyperbranched polyglycerols, dPGs), make it possible to tune the density of ionic and cross-linking groups by synthesis[11]. In this way, fundamental limitations of previous OEIPs can be addressed: swelling and rigidity of the polymer network can be controlled by cross-linking; and transport of "larger" or reactive aromatic substances can be facilitated by tuning the void fraction distribution and effective porosity of the bulk. Importantly, dPG-based polyelectrolytes enable processing from a "one-pot" 3-component mixture of synthesized dPG, crosslinker, and photoinitiator dissolved in methanol. One-pot mixing enables a homogeneous distribution of bulk charge and crosslinking in the membrane, and further offers a high degree of compatibility with a variety of patterning processes such as printing or lithographic techniques.

In this work, the cross-over of molecular delivery technology to plant applications and the capability of transporting aromatic compounds enabled by the newly-developed dPG-based polyelectrolyte is also discovered, FIG. 1b,d. OEIP devices were prepared by photolithographic patterning of the cationically-functionalized dPG film (2 μm thick) on a flexible PET plastic substrate. The shape and dimensions of the resulting OEIP device structure are illustrated and pictured in FIG. 1a,c.

Mass spectrometry was used to quantify the capability of dPG-based OEIPs to transport IAA. In this regard, IAA played the dual role biologically-relevant plant hormone and model aromatic substance. The OEIP was operated continuously at 1 μA and samples were collected in 15 min intervals for 135 min. FIG. 2 shows the summed amounts of measured IAA vs. time. Under these conditions, OEIP operation was observed to achieve an averaged IAA delivery rate of $0.45 \pm 0.16$ pmol min$^{-1}$, corresponding to nanomolar concentrations in close proximity to the delivery tip. For example, 10 pmol of IAA delivered to a 50 μl volume corresponds to a concentration of 200 nM in 15 min. These results indicate that the cationic dPG polymer material system is capable of transporting IAA in biologically active quantities[12]. Trace amounts of 2-oxindole-3-acetic acid (oxIAA), a known IAA catabolite[13], were also detected during mass spectrometry measurements, typically in concentrations 100-1000× lower than the measured IAA. However, oxIAA has been reported to be inactive in previous bioassays[13].

The dPG-based OEIPs were used for in vivo experiments on a highly accessible model plant system suitable for live-cell imaging in the intact organism. Specifically, the apical root meristem and early elongation zone of four-day-old Arabidoposis thaliana seedlings positioned on agar gel were targeted for delivery of IAA via the OEIP. Root tips were monitored using a horizontally oriented Nikon AZ100 spectral macro-confocal laser-scanning microscope system schematically illustrated in FIG. 3a. In this arrangement, seedlings were positioned and imaged vertically.

The root apical meristem of A. thaliana seedlings with IAA (FIG. 2b,c), were targeted using the OEIP devices. Root growth was used as a rapidly accessible parameter to demonstrate the physiological activity of OEIP delivered IAA. It is well established that increased levels of IAA inhibit root growth[12,14]. As a negative control, benzoic acid[15] was delivered by the OEIP device, operated in the same configuration.

FIG. 4b shows bright field images taken of the OEIP device and seedling root tips at the beginning, and after 60 min, of delivery of IAA or benzoic acid. Root tip position was measured at 15-min intervals and averaged over 5 trials, and the growth rate of roots targeted with IAA was compared to benzoic acid negative control and non-targeted A. thaliana seedlings. For seedlings targeted with IAA, a rapid decrease in growth rate was observed starting at 15 min of delivery, from $4.7 \pm 1.0$ μm min$^{-1}$ to $2.4 \pm 0.7$ μm min$^{-1}$ after 60 min, while both benzoic acid and non-targeted control seedlings maintained their growth rates (FIG. 4a). The reduction in growth rate of plant seedlings by delivery of IAA via the OEIP is consistent with previous findings on exogenous application of IAA[12].

To detect, visualize and monitor IAA delivery in near real-time, two widely used engineered transgenic A. thaliana lines were utilized expressing the semi-quantitative DII-Venus[16] or DR5rev:GFP[17] fluorescent auxin-response reporters, both of which are dynamically sensitive to the presence of IAA. The DII-Venus reporter is characterized by absence or reduction in fluorescent signal intensity in the presence of auxin or increasing auxin levels, respectively. Conversely, in DR5, the presence or gain of fluorescent signal intensity indicates presence or increase of auxin concentrations, respectively. The relative auxin abundance is visualized faster by DII-Venus than by DR5[15], because the DII-Venus signal relies on a protein degradation mechanism rather than the slower transcriptional and translational production mechanisms of DR5.

Using DII-Venus seedlings, the fluorescent signal intensity was monitored and onset of strong fluorescence reduction was observed between 30 to 60 min (FIG. 5a,b). Similar roots targeted with the control molecule benzoic acid preserved their fluorescence. Quantitative analyses comparing normalized fluorescent intensities of DII-Venus seedlings targeted with IAA or benzoic acid, as well as non-targeted controls, revealed a strong and significant decrease in fluorescence only after IAA delivery via the OEIP (FIG. 3b).

In the second experiment, the dPG-based OEIP was used to target the elongation zone of DR5rev:GFP reporter seedlings with IAA. Confocal images of the root elongation zone cells revealed the onset of fluorescence in plant tissues after 1 hour and the signal continued to increase between 2 and 3 hours (FIG. 5c). From the image sequence and lateral intensity profile, significant variation in the lateral fluorescent intensity can be observed—with cells on the left side (OEIP side) of the root being brighter than those on the right. Roots targeted with the control molecule benzoic acid, did not display alterations in fluorescent intensity of the DR5 reporter.

In this study fabricated organic electronic devices were fabricated from a newly developed hyperbranched dendritic core-shell polyelectrolyte system that addresses many of the previous limitations of OEIPs and other "iontronic" technologies. The hyperbranched dendritic polyglycerols (dPG) polyelectrolyte system overcomes the limited control of material parameters such as porosity, swelling, and processability. The resulting dPG-based OEIP devices were used to demonstrate delivery of the aromatic plant signaling hormone IAA auxin to elicit rapid physiological changes in developing *Arabidopsis thaliana* roots. Further, the induction of dynamic auxin-response alterations measured by two different fluorescent auxin reporters in transgenic *A. thaliana* seedlings was demonstrated. In addition to the natural auxin hormone IAA, the aromatic delivery capability of the dPG-based OEIP devices was also verified with the synthetic auxin analog 1-NAA. Given that the majority of plant hormones such as abscisic acid, brassino steroids, gibberellins, and cytokinins all include cyclic or aromatic molecular structures, this work provides the foundation for organic electronic devices that interact with plants' fundamental chemical signaling systems with unprecedented spatial and temporal resolution. This technology will be used to test a range of previously known bioactive molecules and observe their effect on plant growth and behavior at previously unattainable length and time scales. This new technology is anticipated to be the starting point for more sophisticated tools to precisely regulate the chemical signaling networks in—and between—living plants and other living systems.

Methods Summary

The invention provides a method for manufacturing an ion-conducting membrane filled with crosslinked hyperbranched polymer electrolytes, which may comprise the steps of:
i) providing a solution comprising a hyperbranched polymer having polymerizable groups and groups that are ionic or ionizable
ii) depositing said solution on a support
iii) crosslinking said hyperbranched polymer.

One method for forming the crosslinked hyperbranched polymer is through a photo-initiated radical coupling, preferably in inert atmosphere to generate stable covalent groups forming the membrane/gels. The general method may then comprise the steps of:
(A) providing a solution of a hyperbranched polymer having polymerizable groups and groups that are ionic or ionizable and a solvent,
(B) mixing said solution with a photoinitiator and crosslinker;
(C) deposit a support with the mixture of step (B);
(D) crosslinking an electrolyte-membrane support and irradiating the electrolyte-membrane with ultraviolet rays; and
(E), removing byproduct on the surface of the membrane, support after the crosslinking step.

More particularly, the invention provides a method for manufacturing an ion-conducting membrane filled with crosslinked hyperbranched polymer electrolytes, comprising the steps of: (A) mixing the hyperbranched polymer comprised with chemical formula 1, 2, 3, a solvent, which may be deionized water, methanol, ethanol, propanol, NMP, DMSO, DMF; (B) mixing 0.1 to 10 parts by weight of a photoinitiator and crosslinker with respect to 100 parts by weight of the mixed solution; (C) deposit a support with support with the solution; (D) crosslinking an electrolyte-membrane support by coating the electrolyte-membrane on a polyethylelenterephthalate (PET) film and irradiating the electrolyte-membrane with ultraviolet rays at an intensity of 30 to 150 mJ/cm2; and (E), removing any byproducts present on the surface of the membrane, support after the crosslinking step.

The hyperbranched polymer may for instance be a so called dendritic hyperbranched polyglycerol (dPG). The photoinitiator may for instance be Thiocure 1300 and the crosslinker may for instance be Irgacure 2959. This means that through the inventive method, and a so called "one-pot 3-component mixture" an OEIP can be very easily manufactured. The need for subsequent treatments before use, is very limited if at all required.

The primary advantages of the proposed concept/s over existing materials are simplicity, potential for low-cost devices and tunable sensitivity of material properties. The main application for the functionalized dPG membranes are drug-delivery, where bio-active molecules are delivered by OEIP (electrophoretic) selective transport.

The second advantage is the one-pot 3-component mixture itself. The mixture, dPGs:Irgacure:Thiocure, in water or methanol, is easily to deposited on many types of surfaces, more importantly, with a homogenic bulk of charge and crosslinks after UV-Curing.

The invention further provides in the alternative a method for manufacturing a meta-stabel gel or aggregates in a solution, comprising the crosslinked hyperbranched polymer electrolytes, which may comprise the steps of:
a) providing a hyperbranched polymer having polymerizable groups and groups that are ionic or ionizable;
b) adding a cross-linking agent to said hyperbranched polymer;
c) adding an initiator to hyperbranched polymer and said cross-linking agent;
d) dissolving said hyperbranched polymer, said cross-linking agent and said initiator in a solvent solution thereby forming a reagent solution; allowing said hyperbranched polymer, said cross-linking agent and said initiator in said reagent solution to react with each other thereby forming a solution comprising said crosslinked hyperbranched polymer.

In the above described method the step e) of allowing said hyperbranched polymer, said cross-linking agent and said initiator in said reagent solution to react with each other, may be performed in a reaction container which is degassed and heated for a specific time.

A dendrolyte may thus be added to a container solution, wherein the solution may be any one of water, alcohols, DMSO, DMF, together with a crosslinker. The crosslinker or crosslinkers may be any molecule having a linear or branched structure, containing two or more functional groups, capable of radical or chemical reactions with the defined dendrolyte. Examples are allyl, acrolyte ones, sulfur based ones "thiocure" or amine ones "diaminbutan (DAB) and a radical initiator. The reaction container is degassed and heated for a specific time. After all reactants have reacted, the excess solvent is removed, and the product isolated as a gel. The purified gel may then be used as active ion-selective membranes for electrophoretic ion-pumps. The meta-stable gel or network may thus be shifted into a more stable solid gel, i.e. through a concentration increase of the supermolecular network.

The ion conducting membrane filled with crosslinked hyperbranched polymer electrolytes or the solution comprising the cross-linked hyperbranched polymer according to the present invention can be used widely in the industrial field of fuel cells, electrophoresis, microfluidics, bio-printing.

Synthesis of polyelectrolytes having polymerizable groups is generally complicated. Direct polymerization to form a polymer having polymerizable groups requires monomers having two different types of polymerizable groups, one forming the polymer, and the other type not taking part in the polymerization reaction, but remaining unreacted for later cross-linking. This requires a high selectivity of polymerizability between the groups, or the use of different types of polymerizing groups. Molecules having both acrylic groups and epoxide groups is a common example of monomers that can form a polymer having polymerizable groups. However, epoxide polymerization is not suited in the presence of ionic groups, such as in a polyelectrolyte.

The alternative, synthesis of a polyelectrolyte having functional groups, followed by a substitution reaction whereby the functional groups are replaced by polymerizable groups is complicated by the fact that most polyelectrolytes are soluble only in water or alcohols, media in which such substitution reactions are difficult to carry out.

Dendrimers consisting of ether bonds, and having hydroxyl terminal groups are on the other hand soluble in solvents suitable for a wide range of substitution reactions, in contrast to unbranched polymers having hydroxyl groups. The latter type of polymers are difficult to dissolve in other media than water or strong acids, media in which substitution reactions leading to polymerizable groups are difficult to carry out, while hydroxyl-terminated dendrimers can be dissolved in a variety of solvents.

In ion-pumps, the ion transport medium can be exposed to extreme pH values. This calls for the use of polymers and cross-links of made up of bond that are stable to hydrolysis. We have used dendrimers built up of ether bonds and cross-linking reactions leading to carbon-carbon bonds to ensure that the ion-transport medium is not hydrolyzed under conditions of ion-pumping.

Molecules that have been successfully pumped using the above described polyelectrolyte as an ion conductive channel or membrane in an ion pump device are monavalent or divalent atomic ions such as H+, Na+, K+ and Cl−. Aromatic molecules such as indole-3-acetic-acid (IAA, auxin), plant hormone, 1-naphthaleneacetic acid (1-NAA), plant hormone analog, naphthalene-2-acetic acid (2-NAA), plant hormone analog, benzoic acid, aromatic control substance, cytokinin, and plant hormone.

EXAMPLES

Hyperbranched Dendritic Polyglycerol (dPG) Synthesis, dPG Membrane and OEIP Device Preparation Circular polyethylene terephthalate (PET) substrates (Policrom Screens) with diameter 101.6 mm (4 inch) were washed with acetone and water and subsequently dried at 110° C. for 10 min before they were treated with $O_2$ plasma (150 W, 60 s). The activated substrates were spin-coated with a 2 mL solution of 5% (3-glycidyloxypropyl)trimethoxysilane (GOPS, Alfa Aesar) in water at 500 rpm for 30 s and allowed to rest in open air for 15 min. The surfaces were washed with ethanol (EtOH) and dried at 110° C. for 10 min. Treated surfaces were spin-coated with 2 ml MeOH stock solution containing 264 mg of dPG (compound 4 in Supplementary Information), 18 mg Thiocure 1300 (Bruno Bock Chemische Fabrik GmbH & Co) and 18 mg Irgacure 2959 (Sigma-Aldrich). UV crosslinking was carried out under nitrogen atmosphere inside a glove box and the films were exposed to UV light (254 nm) for 10 min.

Ion channels were patterned utilizing photolithography of Microposit S1818 photoresist, and developed for 60 s in MF319 (both supplied by Shipley). Unpatterned, cross-linked dPG polymer was removed utilizing a $CF_4+O_2$ reactive ion etch (150 W, 90 s) and remaining photoresist was removed with acetone. To facilitate ion exchange, patterned wafers were soaked in 1 M NaCl(aq) for 5 min. OEIPs were encapsulated with 2×10 μm bar-coated DuPont 5018 UV curing ink. Individual OEIP devices were cut out and packaged in ADW-400 heat shrink tubing containing sealant glue (Kacab Teknik AB). The OEIP delivery tips were shaped by hand using a scalpel.

To hydrate the dPG polyelectrolyte channel, OEIP devices were soaked and stored in deionized water prior to use. Additionally, to reduce the amount of unreacted polymers and chemical compounds remaining in the polyelectrolyte after the above processing steps, OEIP devices were preconditioned by operating the device with 0.1 M KCl(aq) in both the target and source reservoirs. Following the KCl flushing, OEIP devices underwent a loading phase to exchange the Cl⁻ ions in the polyelectrolyte with IAA⁻, OEIPs were operated continuously at 250 nA until steady voltage characteristics were observed (approximately 12 h).

Plant Material and Growth Conditions

*Arabidopsis thaliana* seedlings expressing the auxin-responsive fluorescent markers 35S:DII-Venus[16] or DR5rev:GFP[17] were used to monitor the response of IAA delivered via OEIP. To this end, seeds of both genotypes and wild-type Col-0 were surface sterilized with 70% ethanol for 1 min, incubated in pool cleaner (Biltema, Sweden; one tablet per 2000 ml $H_2O$) for 12 min, and washed four times with sterile, distilled water ($dH_2O$). After 3 days at 4° C. in the dark, seeds were plated and grown on ½ Murashige and Skoog (MS) (Duchefa Biochemie, Haarlem, The Netherlands), 0.5 g/L 2-(N-morpholino)ethanesulfonic acid (MES, Sigma-Aldrich), 1% sucrose, 0.7% plant agar (Duchefa) growth medium plates (120×120 mm square petri-dishes; Gosselin) at pH 5.6 in vertical orientation at 23° C. with 16 h of light per day. 12 h prior to the start of the experiments, 4 days post-germination (dpg) seedlings were positioned onto fresh plates of identical MS media composition additionally supplemented with 0.01 M KCl.

Fluorescent Imaging Protocol

A custom reoriented macro confocal laser-scanning microscope with a vertical stage was used to acquire images (Bergman-Labora, Sweden). The macro confocal consisted of a horizontally placed AZ100 macroscope (Nikon, Japan) adapted with a specially built XYZ motorized stage (Prior Scientific fitted by Bergman-Labora) and supplied with diascopic white light and episcopic fluorescence light (Nikon). A climate enclosure with passive humidification was designed to surround the stage area to keep plants in a humid, dark environment. The AZ100 macroscope was connected to a C2+ confocal laser scanning system (Nikon) equipped with lasers for 405 nm, 457/488/514 nm and 561 nm excitation and a transmitted light detector. A coarse manipulator, MM-89 (Narishige, Japan), was attached to the stage for placing and keeping the OEIP at a specific position. A growth agar plate from which the lid was removed was placed vertically on the macroconfocal stage and an OEIP loaded with IAA was placed with the delivery outlet in the growth agar in close proximity of the seedlings. For imaging, a 2× AZ Plan Fluor objective (NA 0.2, WD 45 mm, Nikon) or a 5× AZ Plan Fluor objective (NA 0.5, WD 16 mm, Nikon) were used. Excitation was at 488 nm and emission detected with a 525/50 filter. DII Venus fluorescence intensities from a single layer were normalized to initial intensity, averaged and compared (Standard deviation of the mean). DR5rev:GFP image intensities were summed from 16 z-stack layers with 3 μm spacing. The lateral fluorescent intensity, plotted at the bottom of each image (FIG. 5c), were summed along the y-axis and normalized to the maximum intensity of the image sequence. We tested the OEIP's ability to deliver the synthetic auxin 1-naphthalene acetic acid (NAA), and observed similar dynamic fluorescence quenching in DII-Venus reporter seedlings.

OEIP Operation

Immediately prior to the experiments, the OEIPs were operated in a target solution of $10^{-5}$ M KCl(aq), and the OEIP device tip was kept from drying excessively during sample loading and OEIP positioning. A Keithley 2612b SourceMeter (Keithley Instruments Inc, Cleveland, Ohio, USA) and custom LabVIEW (National Instruments Corporation, Austin, Tex., USA) software was use to source current and record voltage. The OEIP device was turned on immediately prior to the first imaging sequence and operated at a constant electrical current of 1 μA. For these experiments, the OEIP delivery tip was submerged in the MS media in close proximity (100-200 μm) to the root epidermal tissue (FIG. 3b,c) and was held at a fixed position in the growth MS media for the duration of each trial.

Mass Spectrometry Measurement Protocol

The OEIP reservoir was loaded with 80 μL of 10% methanol in $dH_2O$ containing IAA at $10^{-5}$ M concentration. OEIP outlet tip was submerged in target solution of 50 μL of ½ MS Media, pH 5.7 (see Plant growth conditions) without agar, and containing 0.01 M KCl. Poly(3,4-ethylenedioxythiophene) polystyrene sulfonate (PEDOT:PSS) electrodes on a polyethylene terephthalate (PET) substrate (cut from Orgacon F-350 film, AGFA-Gevaert) were used in the source reservoir and the target solution. OEIP pump was operated sourcing a constant current of 1 μA using a Keithley 2612b SourceMeter and custom LabVIEW software. The target solution was collected and replaced with fresh solution every 15 minutes—at time intervals of 15, 30, 45, 60, 75, 90, 105, 120 and 135 minutes. In-between the analyses, the pump was washed with methanol/$dH_2O$ and stored in $dH_2O$. This was repeated five times with the same pump.

To estimate the amount of IAA (and oxIAA) pumped into the target solution, an IAA analysis was performed. Briefly, 20 μL from each target solution was mixed with 500 μL of $dH_2O$ and purified by solid phase-extraction (SPE) using hydrophilic-lipophilic balance reversed-phase sorbent columns (Oasis HLB; 1 cc/30 mg; Waters, Milford, Mass., USA). Prior to purification, 4 μmol of [$^{13}C_6$]-IAA and 4 pmol of [$^{13}C_6$]-oxIAA were added to each sample as internal standards to validate the quantification. Purified samples were analyzed using an LC-MRM-MS (liquid chromatography-multiple reaction monitoring-mass spectrometry) system. The LC-MS system consisted of 1290 Infinity Binary LC System coupled to 6490 Triple Quad LC/MS System with Jet Stream and Dual Ion Funnel technologies (Agilent Technologies, Santa Clara, Calif., USA). Chromatograms were analyzed using MASSHUNTER software version B.05.02 (Agilent Technologies). A Milli-Q deionization unit (Millipore, France) was used for preparation of the purified water for mobile phases and solutions. [$^{13}C_6$]-oxIAA was obtained from Olchemim Ltd (http://www.olchemim.cz/). All other chromatographic solvents and chemicals were of analytical grade or higher purity from Sigma-Aldrich Chemie GmbH (Steinheim, Germany).

Synthesis Meta-Stable Gel or Aggregates in a Solution Comprising of Hyperbranched Dendritic Polyglycerol (dPG)

Polymer (1.715 mmol, 1 eq.) was added together with Thiocure ETTMP 1300 (0.345 mmol, 0.2 eq.) and initiator AIBN (0.345 mmol, 0.2 eq.) into a micro tube. The reagents was dissolved with deaerated DMSO (3 mL), the container was sealed with a cap and purged for 30 min with $N_2$-gas. The reaction tube was then directly submerged into a 70-80° C. oil bath and left to stir overnight (16 h) until the reaction was quenched with deionized water and the solvents was evaporated. The product was dissolved in methanol and dialyzed with a Regenerated Cellulose tube 3.5 kDa pore selectivity in methanol.

REFERENCES

1. LaVan, D. A., McGuire, T. & Langer, R. Small-scale systems for in vivo drug delivery. Nat. Biotechnol. 21, 1184-1191 (2003).
2. Abidian, M. R., Kim, D. H. & Martin, D. C. Conducting-polymer nanotubes for controlled drug release. Adv. Mater. 18, 405-409 (2006).
3. Xu, Q. et al. Preparation of monodisperse biodegradable polymer microparticles using a microfluidic flow-focusing device for controlled drug delivery. Small 5, 1575-1581 (2009).
4. Svirskis, D., Travas-Sejdic, J., Rodgers, A. & Garg, S. Electrochemically controlled drug delivery based on intrinsically conducting polymers. J. Control. Release 146, 6-15 (2010).
5. Isaksson, J. et al. Electronic control of Ca2+ signalling in neuronal cells using an organic electronic ion pump. Nat. Mater. 6, 673-679 (2007).
6. Tybrandt, K. et al. Translating electronic currents to precise acetylcholine-induced neuronal signaling using an organic electrophoretic delivery device. Adv. Mater. 21, 4442-4446 (2009).
7. Simon, D. T. et al. Organic electronics for precise delivery of neurotransmitters to modulate mammalian sensory function. Nat. Mater. 8, 742-746 (2009).
8. Jonsson, A. et al. Therapy using implanted organic bioelectronics. Sci. Adv. 1, e1500039-e1500039 (2015).
9. Stavrinidou, E. et al. Direct measurement of ion mobility in a conducting polymer. Adv. Mater. 25, 4488-93 (2013).
10. Astruc, D., Boisselier, E. & Ornelas, C. Dendrimers designed for functions: From physical, photophysical, and supramolecular properties to applications in sensing, catalysis, molecular electronics, photonics, and nanomedicine. Chem. Rev. 110, 1857-1959 (2010).
11. Sunder, A., Hanselmann, R., Frey, H. & Mülhaupt, R. Controlled synthesis of hyperbranched polyglycerols by ring-opening multibranching polymerization. Macromolecules 32, 4240-4246 (1999).
12. Rahman, A. et al. Auxin, actin and growth of the Arabidopsis thaliana primary root. Plant J. 50, 514-528 (2007).
13. Pencik, A. et al. Regulation of Auxin Homeostasis and Gradients in Arabidopsis Roots through the Formation of the Indole-3-Acetic Acid Catabolite 2-Oxindole-3-Acetic Acid. Plant Cell 25, 3858-3870 (2013).

14. Grieneisen, V. a., Xu, J., Margée, A. F. M., Hogeweg, P. & Scheres, B. Auxin transport is sufficient to generate a maximum and gradient guiding root growth. Nature 449, 1008-1013 (2007).
15. Geisler, M., Wang, B. & Zhu, J. Auxin transport during root gravitropism: transporters and techniques. Plant Biol. 16, 50-57 (2014).
16. Brunoud, G. et al. A novel sensor to map auxin response and distribution at high spatio-temporal resolution. Nature 482, 103-106 (2012).
17. Friml, J. et al. Efflux-dependent auxin gradients establish the apical-basal axis of Arabidopsis. Nature 426, 147-153 (2003).

The invention claimed is:

1. A device for transport of ions and/or charged molecules between a source and a target electrolyte, comprising:
    a first electrode provided at or in said source electrolyte and a second electrode provided at or in said target electrolyte; wherein said first and second electrodes provides an electrical control of an ion flow;
    an ion- and/or permselective polyelectrolyte between said source electrolyte and said target electrolyte configured to transport ions and/or charged molecules via electrophoresis and to function as an ion-selective membrane; and
    a voltage application system configured to apply a voltage and maintain a potential difference between said source and said target electrodes to effect ion transport from said source to said target electrode;
    wherein said polyelectrolyte comprises a hyperbranched polyglycerol polymer that has been cross-linked,
    wherein said hyperbranched polyglycerol polymer prior to crosslinking comprises D, L and T units, the L and T units comprising both polymerizable groups and ionic or ionizable groups, wherein the polymerizable groups and the ionic or ionizable groups are selected from (meth)acryloxy, (meth)acrylamido, vinyl, sulphonate, phosphonates, carboxylates, ammonium, and phosphonium;
    the polymerizable groups and the ionic or ionizable groups being connected to the L and T units by a connecting group selected from an alkyl group with C1~C20, an aryl group with C6~C20, a heteroaryl group with C2~C20, a cycloalkyl group with C6~C20, and a heterocyclic group with C2~C20.

2. The device according to claim 1, wherein the hyperbranched polyglycerol polymer prior to crosslinking has a degree of branching in the range of 0.05 to 1.

3. The device according to claim 1, wherein the hyperbranched polyglycerol polymer prior to crosslinking has a degree of branching in the range of 0.1 to 1.

4. The device according to claim 1, wherein the hyperbranched polyglycerol polymer prior to crosslinking has a degree of branching in the range of 0.5 to 1.

5. The device according to claim 1, wherein the hyperbranched polyglycerol polymer prior to crosslinking has a degree of branching in the range of 0.7 to 1.

6. A method of delivering ions and/or charged molecules by electrophoretic selective transport, comprising
    providing a device according to claim 1;
    providing ions and/or charged molecules to the source electrolyte; and
    applying a potential difference between the source electrode and target electrode, thereby delivering the ions and/or charged molecules to the target electrolyte.

7. The method according to claim 6, wherein the ions and/or charged molecules being delivered are any one of monovalent and divalent atomic ions, multivalent charged biomolecules, charged aromatic molecules, and nonaromatic charged molecules.

8. The method of claim 6, wherein the ions and/or charged molecules is a drug that is an endogenous substance.

9. The method of claim 6, wherein the hyperbranched polyglycerol polymer prior to crosslinking has a degree of branching in the range of 0.1 to 1.

10. The method of claim 6, wherein the hyperbranched polyglycerol polymer prior to crosslinking has a degree of branching in the range of 0.5 to 1.

11. The method of claim 6, wherein the hyperbranched polyglycerol polymer prior to crosslinking has a degree of branching in the range of 0.7 to 1.

12. The method of claim 6, wherein the hyperbranched polyglycerol polymer prior to crosslinking has a degree of branching in the range of 0.05 to 1.

* * * * *